United States Patent
Mack et al.

[19]

[11] Patent Number: 5,899,360
[45] Date of Patent: *May 4, 1999

[54] MULTI-CHAMBER REFILLABLE DISPENSER

[75] Inventors: Robert Mack, Flemington; James C. McKinney, Cranbury; Kenneth R. Berger, Flemington, all of N.J.

[73] Assignee: Colgate - Palmolive Company, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/647,545

[22] Filed: May 15, 1996

Related U.S. Application Data

[60] Provisional application No. 60/000,089, Jun. 9, 1995.

[51] Int. Cl.⁶ .................................................. B67D 5/00
[52] U.S. Cl. ...................... 222/83; 222/137; 222/145.3; 222/183; 222/184; 222/326
[58] Field of Search ............................ 222/81, 83, 137, 222/145.3, 145.5, 183, 185, 326, 327, 386

[56] References Cited

U.S. PATENT DOCUMENTS

| | | | |
|---|---|---|---|
| D. 277,073 | 1/1985 | Czech | D9/366 |
| D. 306,554 | 3/1990 | Lawson | D9/300 |
| D. 307,113 | 4/1990 | Thompson | D9/373 |
| D. 311,861 | 11/1990 | Vanhoutte | D9/300 |
| D. 313,181 | 12/1990 | Pettengill | D9/403 |
| D. 315,496 | 3/1991 | Pettengil | D9/373 |
| D. 320,735 | 10/1991 | Pettengill | D9/373 |
| 2,661,871 | 12/1953 | Huenergardt | 222/129 |
| 3,166,221 | 1/1965 | Nielsen | 222/137 |
| 3,197,071 | 7/1965 | Kuster | 222/94 |
| 3,200,995 | 8/1965 | Gangwisch | 222/94 |
| 3,207,375 | 9/1965 | Bereziat et al. | 222/81 |
| 3,236,418 | 2/1966 | Dalle et al. | 222/135 |
| 3,402,855 | 9/1968 | Schroeder et al. | 222/83 |
| 3,570,719 | 3/1971 | Schiff | 222/137 |
| 3,613,956 | 10/1971 | McCulloch | 222/136 |
| 4,040,420 | 8/1977 | Speer | 128/218 M |
| 4,046,288 | 9/1977 | Bergman | 222/135 |
| 4,121,739 | 10/1978 | Devaney et al. | 222/137 |
| 4,240,566 | 12/1980 | Bergman . | |
| 4,261,481 | 4/1981 | Speer | 222/135 |
| 4,528,180 | 7/1985 | Schaeffer | 424/52 |
| 4,687,663 | 8/1987 | Schaeffer | 424/52 |
| 4,747,517 | 5/1988 | Hart | 222/137 |
| 4,771,919 | 9/1988 | Ernst | 222/134 |
| 4,773,562 | 9/1988 | Gueret | 222/135 |
| 4,795,043 | 1/1989 | Odet et al. | 222/83 X |
| 4,826,048 | 5/1989 | Skorka et al. | 222/137 |
| 4,871,090 | 10/1989 | Hoffmann | 222/81 |
| 4,974,756 | 12/1990 | Pearson et al. | 222/562 |
| 5,020,694 | 6/1991 | Pettengill | 222/137 |
| 5,038,963 | 8/1991 | Pettengill et al. | 222/145 |
| 5,065,906 | 11/1991 | Maeder | 222/137 |
| 5,224,627 | 7/1993 | Weag | 222/135 |
| 5,289,949 | 3/1994 | Gentile | 222/137 |
| 5,318,203 | 6/1994 | Iaia et al. | 222/94 |
| 5,332,124 | 7/1994 | Cancro et al. | 222/137 |
| 5,335,827 | 8/1994 | Gentile | 222/137 |
| 5,645,193 | 7/1997 | Gentile et al. | 222/137 |

FOREIGN PATENT DOCUMENTS

| | | |
|---|---|---|
| 0294672 | 5/1988 | European Pat. Off. . |
| 0576222 | 6/1993 | European Pat. Off. . |

*Primary Examiner*—Joseph A. Kaufman
*Attorney, Agent, or Firm*—Michael McGreal

[57] ABSTRACT

The dispenser is a rigid type multi-chamber, refillable dispenser where only the substance containing chambers need to be discarded and replaced. At the point of the chambers interconnecting into the upper portion of the dispensers there is a cutter to break the seal on the chambers. In operation stabilized piston rods fit into each chamber and push against pistons having a deformable upper surface to expel the substance. The refill chambers have off-center exit openings whereby the distance to the dispenser nozzle exit is minimized. The push rods are stabilized by being of a size and shape to be proximate the walls of the chambers while actuating the pistons.

23 Claims, 10 Drawing Sheets

MULTI-CHAMBER REFILLABLE DISPENSER

This application claims benefits under provision application Ser. No. 60/000,089 filed Jun. 9, 1995.

BACKGROUND OF THE INVENTION

This invention relates to multi-chamber dispensers for viscous substances that are adapted to receive sets of refill chambers. More particularly, it relates to the dispensing of two or more substances that are not storage stable and thus cannot be contacted or mixed until the time of use.

There is a need in the dental care area for the delivery of two or more substances that are reactive with each other or which to some degree are not storage stable in the presence of each other. This problem is solved by the use of a multi-chamber dispenser where the substances do not contact until dispensed. Examples of such substances are baking soda and various peroxide yielding materials and stannous fluoride and pyrophosphate compounds. There are yet other substances that advantageously are applied to teeth and gums together in order to achieve a particular therapeutic effect that cannot be mixed until the time of use.

There are various types of dispensers that have been used to dispense two or more non-compatible substances. For viscous materials these primarily include tubes and rigid pump dispensers. Illustrative of tube dispensers developed for this purpose are those described in U.S. Pat. No. 1,363,064; U.S. Pat. No. 1,698,404; U.S. Pat. No. 1,699,532; U.S. Pat. No. 2,819,723; and U.S. Pat. No. 3,105,615. In U.S. Pat. No. 1,353,064 there is disclosed side-by-side tubes, two tubes with a longitudinal separatory wall and two tubes created by a horizontal barrier with an opening at each end. U.S. Pat. No. 1,698,404 discloses a tube within a tube. In U.S. Pat. No. 1,699,532 there is shown a variation of a tube within a tube. In U.S. Pat. No. 2,819,723 there is shown a hair dying apparatus consisting of a dispensing comb and brush connected to a two tubes. In U.S. Pat. No. 3,105,615 there is shown a pair of side-by-side aligned tubes.

Another type of multi-chamber dispenser is the rigid pump dispenser. This type of dispenser is illustrated by U.S. Pat. No. 4,040,420; U.S. Pat. No. 4,046,288; U.S. Pat. No. 4,121,739; U.S. Pat. No. 4,747,517; U.S. Pat. No. 4,949,873; U.S. Pat. No. 5,020,694 and U.S. Pat. No. 5,056,906. U.S. Pat. No. 4,040,420 discloses a dual chamber device with two essentially cylindrical cylinders and hand actuated piston rods that separately move the pistons. The product converges at the exit and is co-dispensed. U.S. Pat. No. 4,046,288 discloses a related device where the pistons are moved on threaded piston rods. In U.S. Pat. No. 4,121,739 there is disclosed a particular seal construction on the pistons in a pump dispenser. In U.S. Pat. No. 4,747,517 the two pistons are described to be hemispherical. Related semicircular pistons are shown in U.S. Pat. No. 4,949,873. U.S. Pat. No. 5,020,694 discloses a dispenser where there is added structure to cause the dispensed substances to flow together. In related U.S. Pat. No. 5,395,827 there is disclosed a dual chamber dispenser that is adapted to use refill chambers. These various references illustrate the present state-of-the-art of multi-chamber dispensers, and in particular multi-chamber dispensers and refillable multi-chamber dispensers.

Each of these prior art dispensers has some problems. The tube dispensers do not guarantee a constant flow of each substance. If one tube is squeezed with more force than the other, more of the substance in that tube will be dispensed. This is a significant drawback. In the rigid dispensers the dispenser must be refillable. If not refillable there will be too much waste of plastic packaging. And some units that are refillable do not conserve the use of plastic. In U.S. Pat. No. 5,289,949 the entire top piece that includes a shroud, nozzle and closure are discarded and replaced. Only the lower housing with the piston rods is retained. This conserves little of the plastic of the dispenser.

The present dispenser addresses these issues and solves these problems. The two or more substances are dispensed in given amounts. The only components that are discarded after use are the chambers that contained the substances that have been dispensed. All of the other components are reused. Also, the flow path from the chambers to the dispenser exit is shortened. Pistons with a deformable upper surface are used to more fully expel all of the substances from the chambers. Other features include stabilized piston rods and the automatic puncturing of the seal on the refill chambers when the refill unit is inserted into the dispenser. A cutter located in the upper portion of the dispenser cuts the seal on the chambers and rolls the seal outwardly so that remnants of the seal will not affect the dispensing of the substances. This is automatically accomplished as the set of refill chambers is inserted into the dispenser.

BRIEF SUMMARY OF THE INVENTION

The present dispenser is a rigid type, multi-chamber refillable dispenser for simultaneously dispensing a plurality of substances in a constant ratio, one to another. The dispenser consists of a lower portion and an upper portion. The lower portion holds a piston rod for each of the cylinders in the upper portion. Each of these piston rods preferably is of a shape so that at least two parts of the piston rods are proximate the walls of the chambers when interfitted into the upper portion. This assists in keeping the upper portion and lower portion aligned. The lower part of the lower portion has a foot that extends outwardly at the base to provide additional stability to the dispenser during use.

The upper portion of the dispenser contains the replaceable chambers that contain the substances to be dispensed, a seal means to seal the chambers into the upper portion, and combined with the seal means a cutter to puncture a protective seal on the top of each chamber. The seal means preferably is a projection extending from the inner surface of the upper wall of the upper section. A channel from the seal means connects to the exit of the dispenser which has a hinged closure.

The replaceable chambers preferably are interconnected and inserted as a unit. Each chamber has a piston, optionally with a deformable upper surface. The exit of each chamber comprises a projection, usually cylindrical, and preferably is offset from the center of the chamber so that each chamber exit is in an adjacent orientation. In this way the flow path of the substances from the chambers to the dispenser exit is minimized. This reduces the force to actuate the dispenser.

After the substances in the chambers have been exhausted, the top and bottom portions are detached and the depleted chambers are removed by pulling downwardly on the chambers from the upper portion. These are discarded. A new set of refill chambers is inserted up into the upper portion and with a sustained push a projection on the upper surface of the chambers enters the respective seal means which cuts the cover seal of each chamber and seals the projection of each chamber into the upper portion of the dispenser. The lower portion is then fitted over the upper portion with the piston rods on the lower portion entering each of the chambers in the upper portion. The dispenser is then ready to simultaneously dispense the substances in the chambers in a given ratio.

The stability of the dispenser during use is enhanced by the use of close tolerances at corner portions of the upper portion and lower portion. This results in a close snug fit of the upper portion into the lower portion resulting in a fit with little lateral tilting movement. In this way there is a more uniform dispensing of the substances in each chamber.

The ratio of dispensing the substances can be changed by changing the diameter of a chamber. In this way the ratio of one substance being dispensed to another can be controlled.

DETAILED DESCRIPTION OF THE INVENTION

Figure 1:
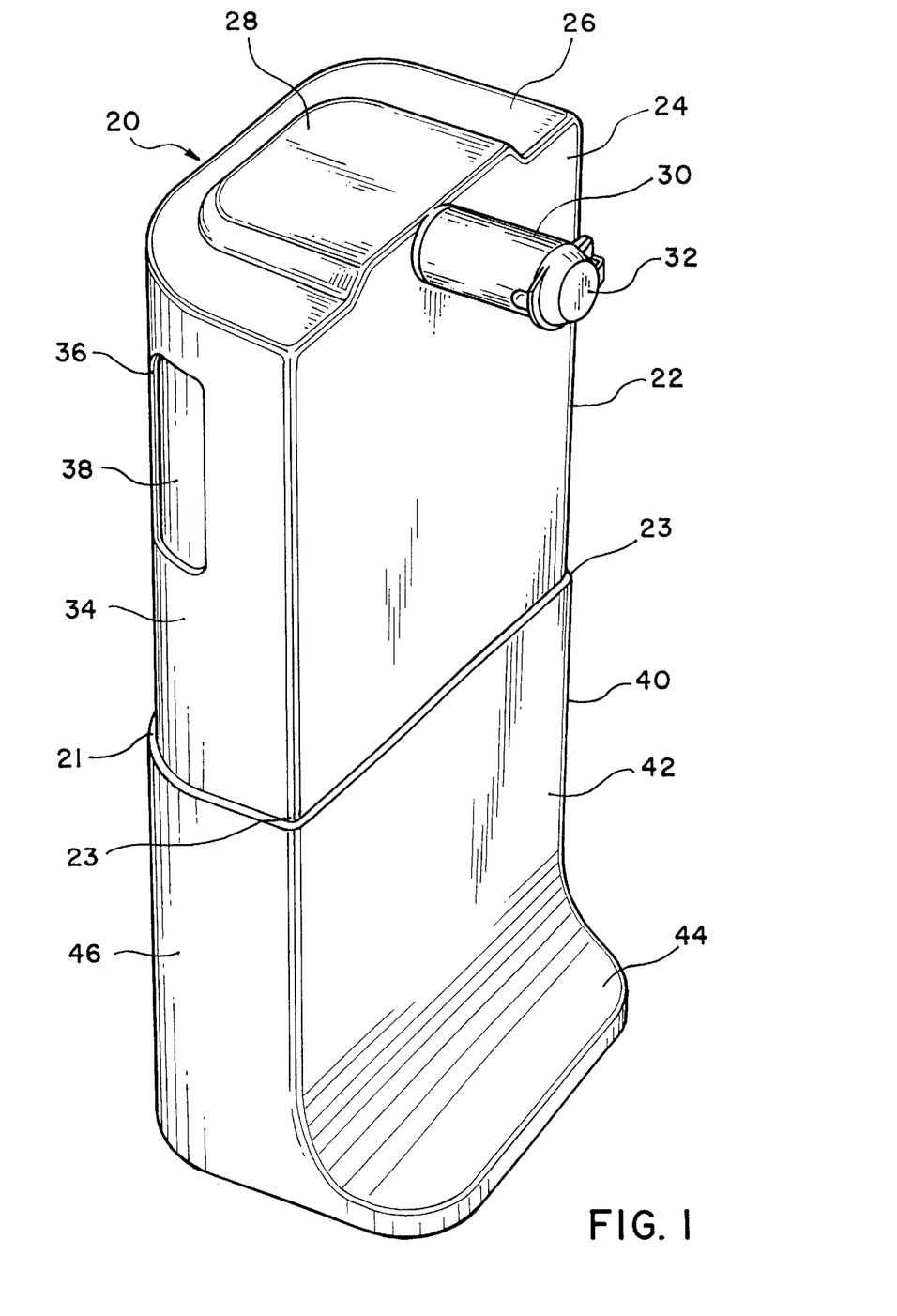
FIG. 1 is a perspective view of the present dispenser.

The multi-chamber refillable dispenser will be described in more detail with reference to the drawings. In FIG. 1, there is shown a perspective view of the dispenser. The dispenser 20 is comprised of upper portion 22 and lower portion 40. The upper portion has front surface 24, top wall 26 and raised push pad 28. Extending from front surface 24 is nozzle 30 with hinged closure 32. Sidewall 34 has a rectangular aperture 36 through which tubular chamber 38 is visible. The lower portion 40 has front surface 42 and an outwardly extending foot 44 which serves to stabilize the dispenser during use. Sidewall 46 of the lower portion is visible in this view.

The upper portion 22 and the lower portion 40 slideably interfit with the upper portion fitting down into the lower portion. The front surface of the upper portion and of the lower portion are essentially flat to having a minor radius. Front corners 23 are in the range of right angles with the rear corners 21 having a wide radius. The close tolerances of the front corners of the upper portion and lower portion and the close interfit aid in orienting and stabilizing the upper portion in the lower portion.

Figure 2:
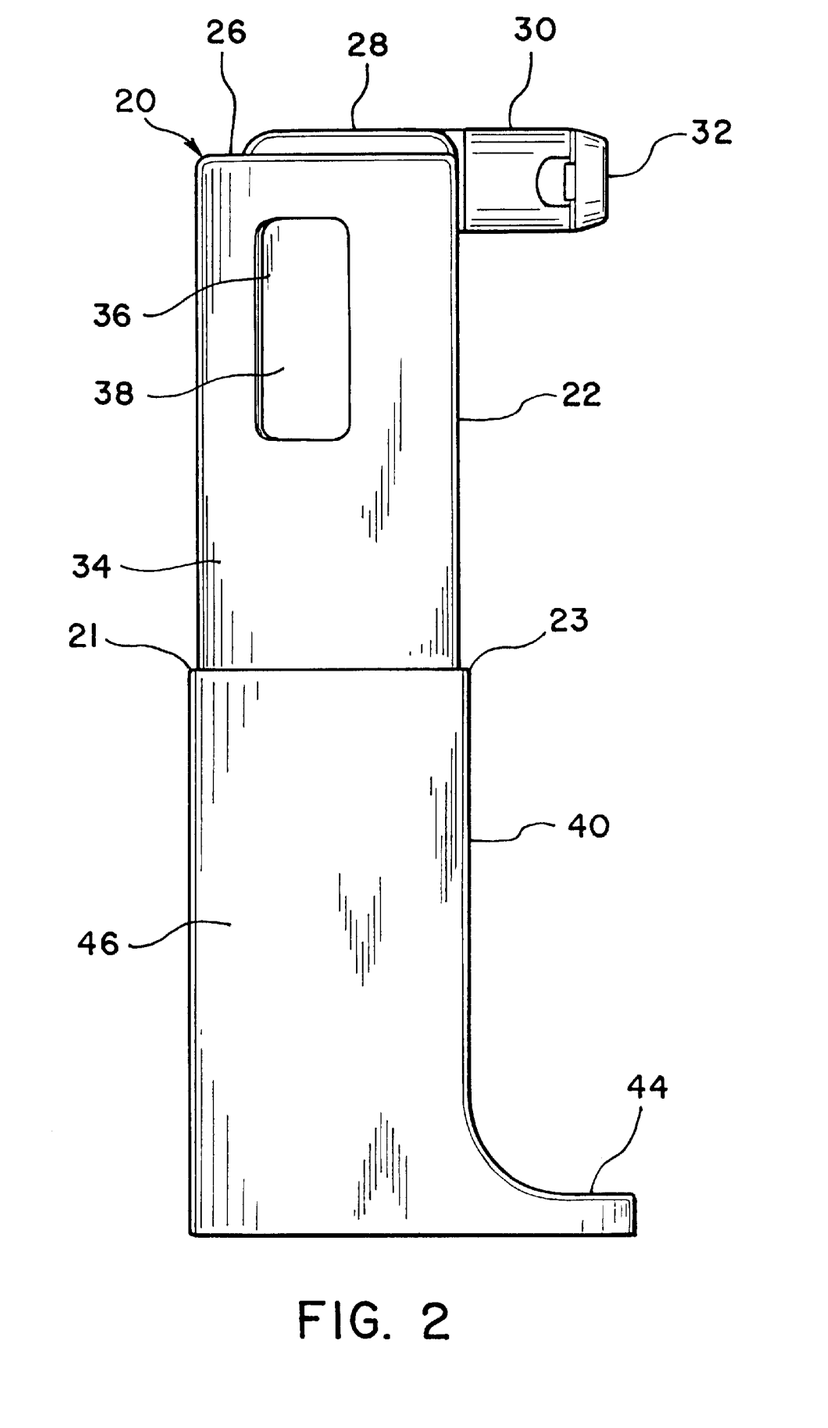
FIG. 2 is a side elevational view of the dispenser.

FIG. 2 is a side elevational view of the dispenser of FIG. 1. This view shows the corners and the foot 44 in more detail.

Figure 3:
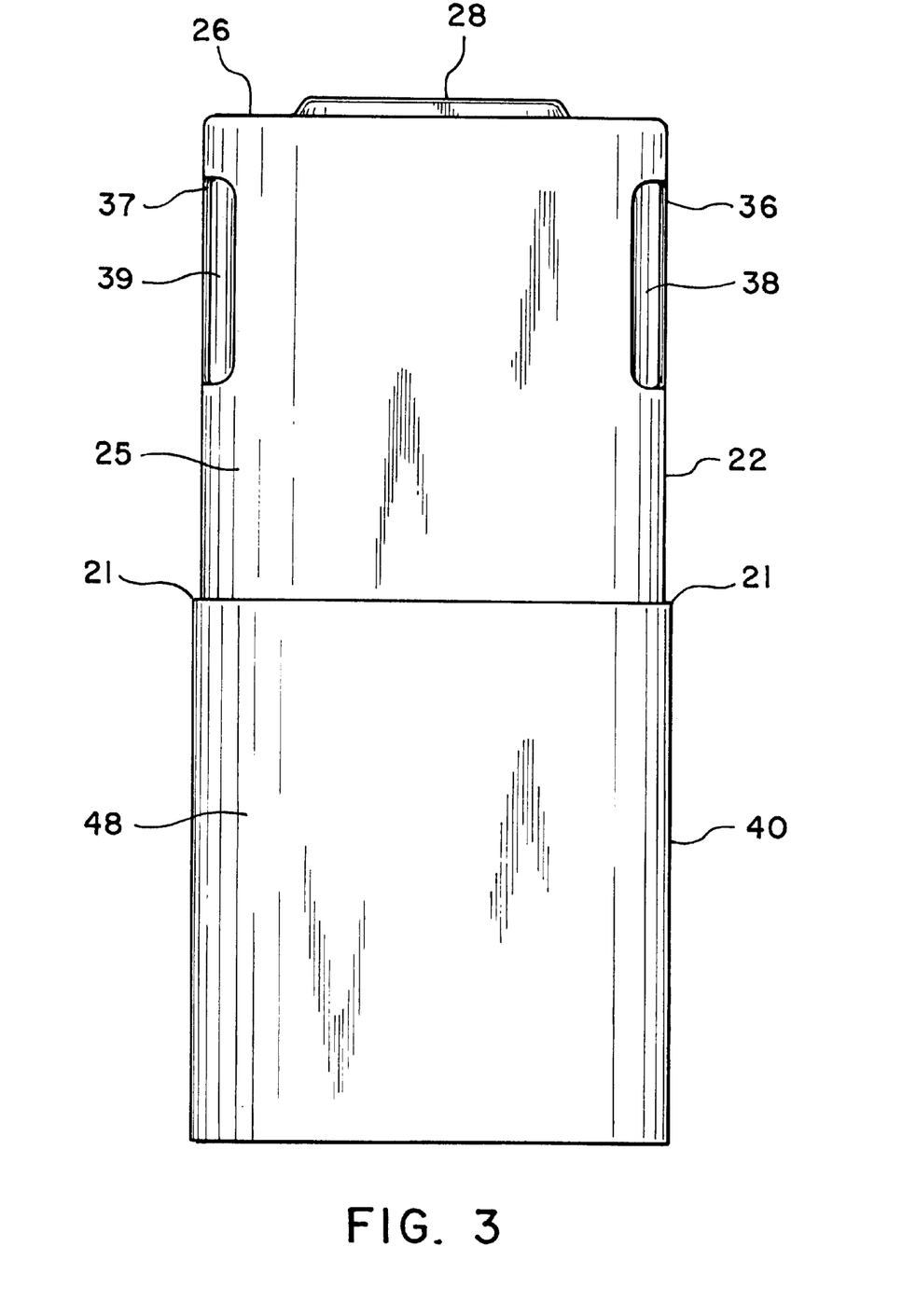
FIG. 3 is a rear elevational view of the dispenser.
Figure 4:
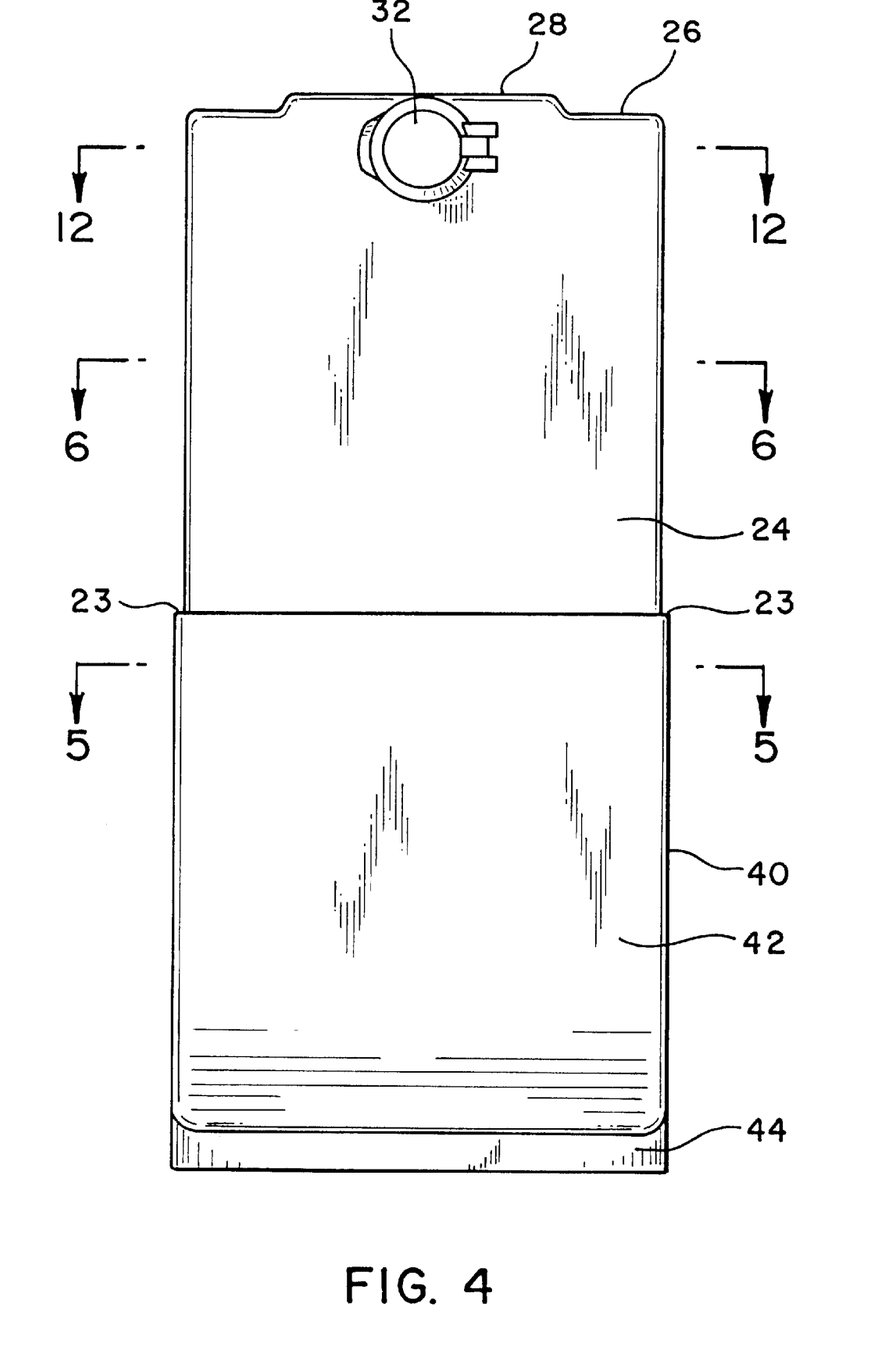
FIG. 4 is a front elevational view of the dispenser.

FIG. 3 is a rear elevational view of the dispenser. In this view there is shown rear wall 48 of the lower portion and rear wall 25 of the upper portion. Also shown is aperture 37 which is of the same shape as aperture 36. Cylindrical chamber 39 which like cylindrical chamber 38 contains a substance to be dispensed is seen through aperture 37. FIG. 4 is a front elevational view of this dispenser.

Figure 5:
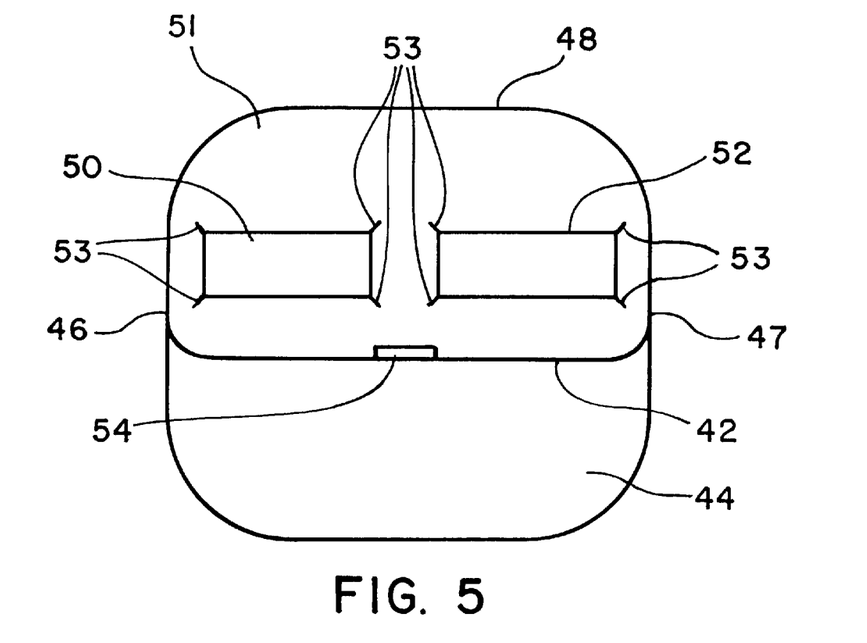
FIG. 5 is a cross-sectional view of the dispenser along line 5—5 in FIG. 4.

FIG. 5 is a cross-sectional view of the dispenser as shown along line 5—5 of FIG. 4. This is a cross-sectional view of the lower portion. There is seen in this view foot 44, side walls 46 and 47 and rear wall 48. Mounted on front wall 42 is projection 54 which interacts with a projection on the upper portion to serve to lock the upper and lower portions together. Piston rods 50 and 52 extend upwardly from the base 51 of the lower portion. These piston rods are shown to be rectangular but can be of various shapes. However, the piston rods must fit into the chambers in the upper portion and optionally at least two portions can be proximate the inner wall of the chamber into which it fits. In this embodiment the corners of the rectangular piston rods are proximate the inner wall of the chambers. In this view, the corners have projecting tips 53 which will contact the inner wall of the cylindrical chambers. These piston rods and the close fit in the tubular chambers assist in stabilizing the upper portion in the lower portions.

Figure 6:
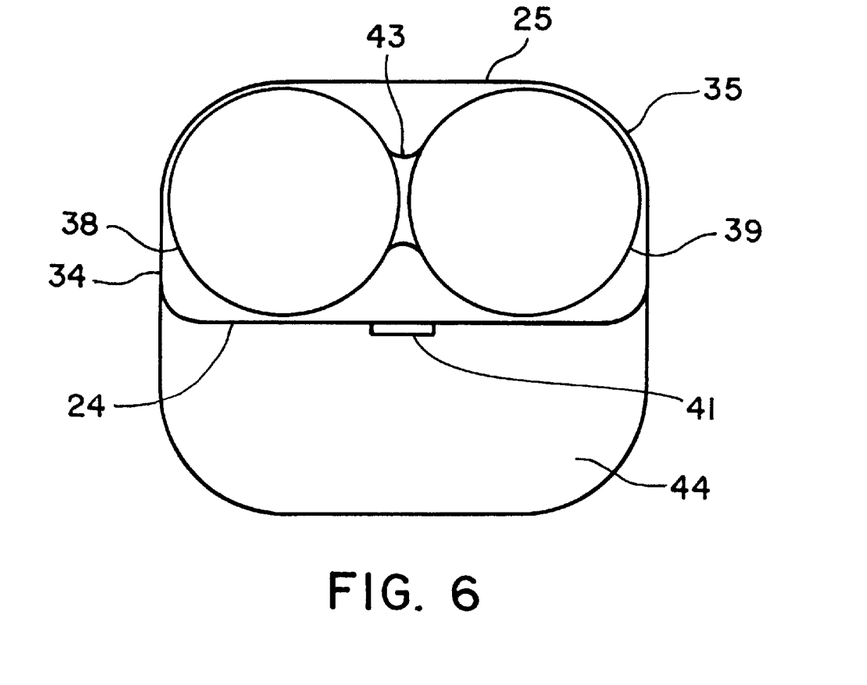
FIG. 6 is a cross-sectional view of the dispenser of FIG. 4 along line 6—6.

FIG. 6 is a cross-sectional view of the dispenser of FIG. 4 along line 6—6. There is shown tubular chambers 38 and 39 which are interconnected by web 43.

Sidewalls 34 and 35, rear wall 25 and front wall 24 enclose the tubular chambers. Front wall 24 has projection 41 which interacts with projection 54 of the upper portion to lock the upper portion and lower portion together.

Figure 7:
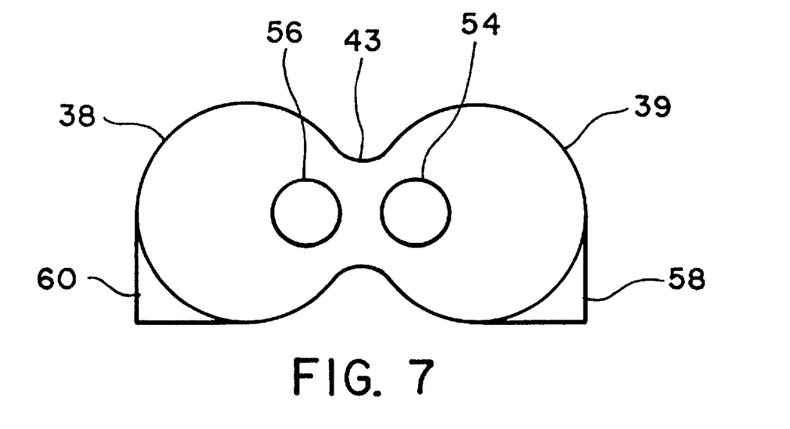
FIG. 7 is a top plan view of the refill chambers.

FIG. 7 is a top plan view of the tubular chambers attached together so that they are inserted into the upper portion in one unit. This view shows cylindrical cylinders 38 and 39 connected by web 43. Each chamber has an offset cylindrical exit aperture. Tubular chamber 38 has aperture 56 and tubular chamber 39 aperture 54. Extensions 58 and 60 serve to interact with corners 23 of the upper portion to orient and stabilize the chambers in the upper portion.

Figure 8:
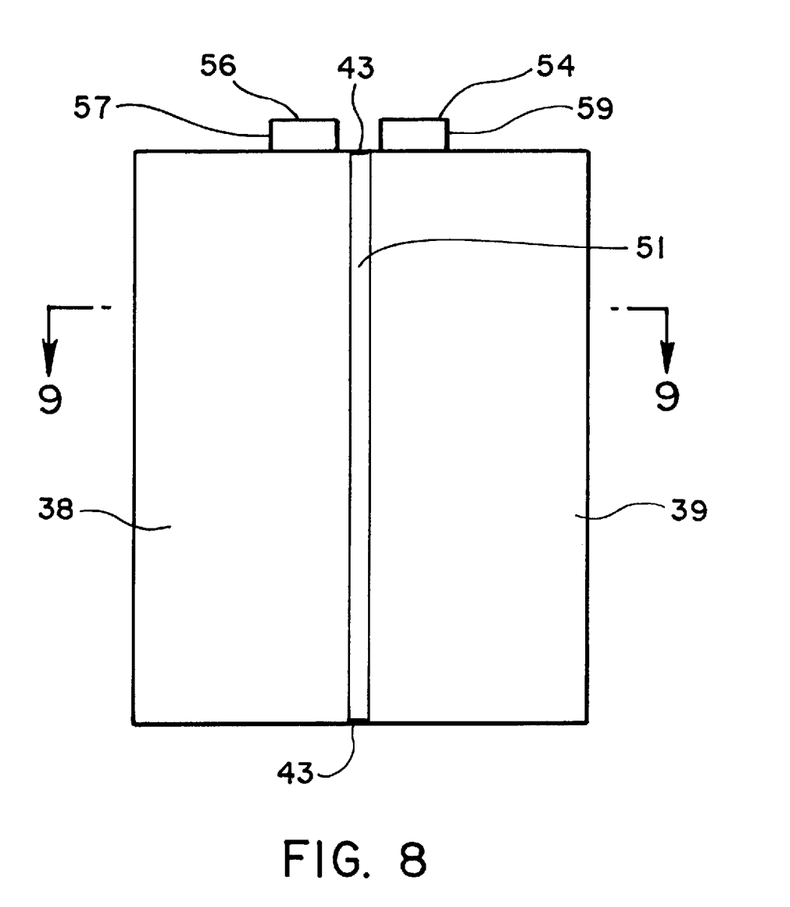
FIG. 8 is a side elevational view of the refill chambers.

FIG. 8 is an elevational view of a refill unit for the dispenser. There are shown tubular chambers 38 and 39 connected by web 43. There is an open space 51 between the chambers. Cylindrical projections 57 and 59 project from tubular chambers 38 and 39 respectively. These tubular chambers will usually contain different substances. These substances will exit through apertures 54 and 56.

Figure 9:
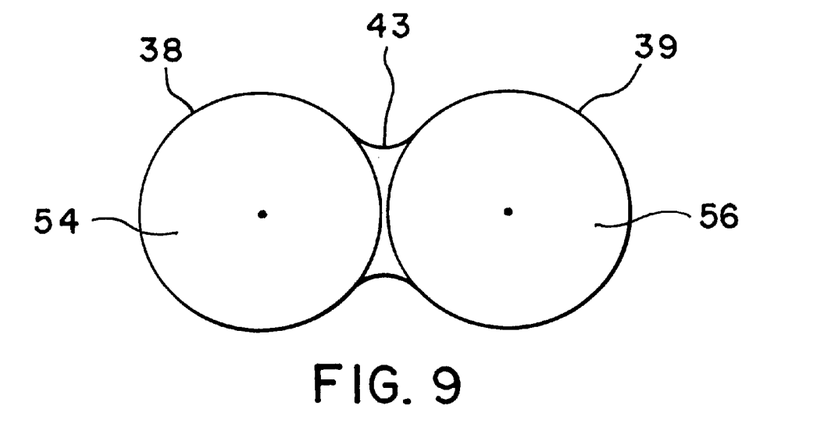
FIG. 9 is a cross-sectional view of the refill chambers of FIG. 8 along line 9—9.

FIG. 9 is a cross-sectional view of the tubular chambers of FIG. 8 along line 9—9. There is shown pistons 54 and 56 in tubular chambers 38 and 39 respectively.

Figure 10:
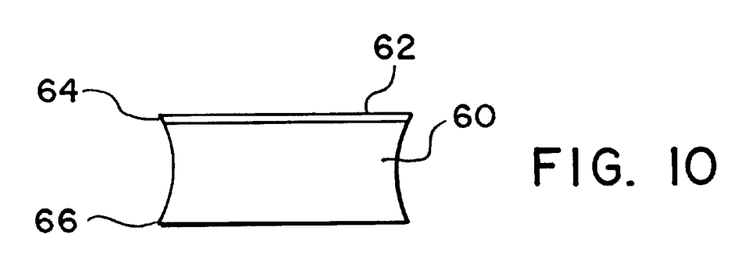
FIG. 10 is a side elevational view of a piston.

FIG. 10 is an elevational view of a piston. There is a main body portion 60 which has a deformable top portion 62. This deformable top portion can be of any elastomeric material that will conform to the shape of the top of a cylindrical chamber. Foamed plastics are particularly useful and in particular closed cell polymeric foams that can extend up into cylindrical projections 57 and 59. Edges 64 and 66 are contact edges. These edges contact the inner surface of each tubular cylinder and move along the inner surface during dispensing. They also maintain the substance being dispensed above each piston.

Figure 11:
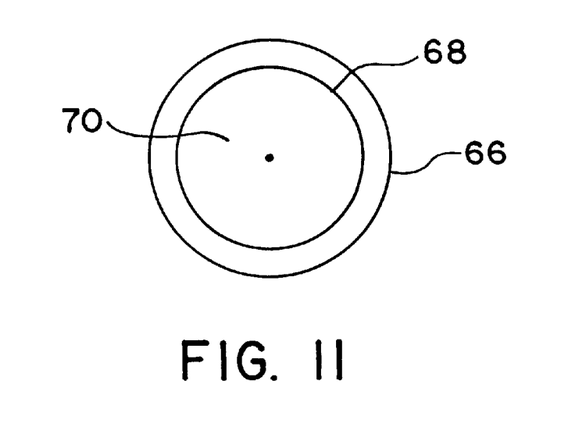
FIG. 11 is a bottom plan view of a piston.

FIG. 11 is a bottom plan view of a piston. The surface 70 has cylindrical projection 68 which extends downwardly to the region of edge 66. It is this cylindrical projection 68 that is contacted by the piston rods when the piston is actuated. Consequently this cylindrical projection should not deform during dispensing.

Figure 12:
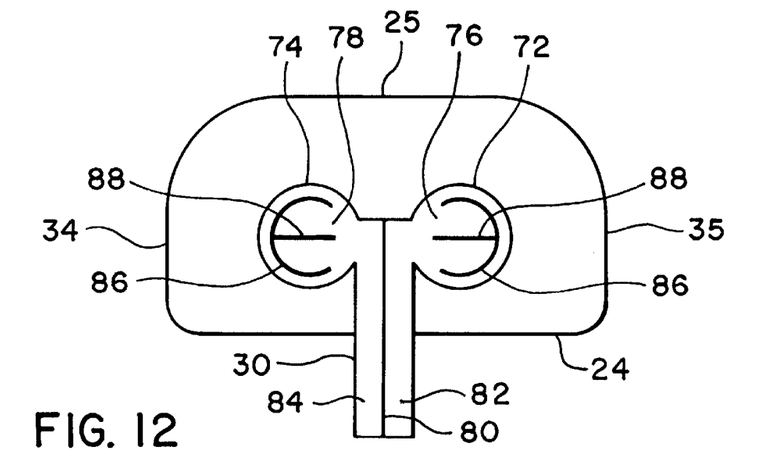
FIG. 12 is a cross-sectional view of the dispenser of FIG. 4 along line 12—12.

FIG. 12 is a cross-sectional view of the head part of the upper portion along line 12—12 of FIG. 4. There is shown sidewalls 34 and 35, rear wall 25 and front wall 24. Depending from the inner surface of—the top wall are seal cylindrical projections 72 and 74. Region 78 provided by seal cylindrical projection 74 communicates with channel 84 of spout 30 and region 76 provided by seal cylindrical projection 76 communicates with channel 82 of spout 30. Dividing wall 80 keeps the channels separated. Each of regions 76 and 78 has a cutter mechanism to puncture the seal on the cylindrical projection of a tubular chamber as the tubular chamber cylindrical projections fit up into the seal cylindrical projections 74 and 76 moves with the film to the side so that the flow of paste is not impeded. The cutter is comprised of a semicircular projection 86 which has a planar end surface and a triangular section 88 located in the semicircular projection. The triangular tip of this triangular section will extend below the plane of the semicircular projection.

Figure 13:
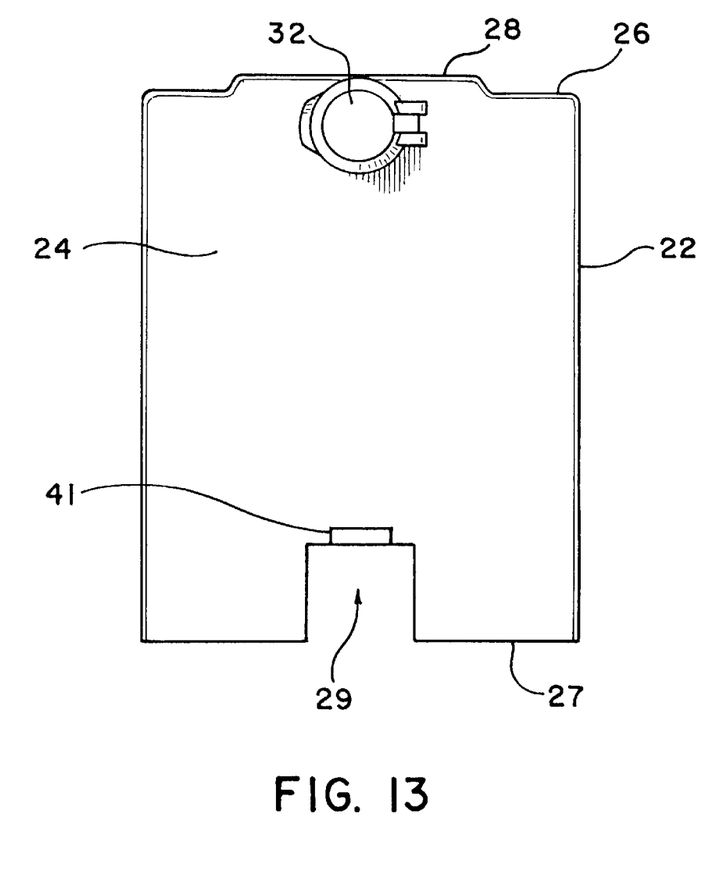
FIG. 13 is a front elevational view of the upper portion.

FIG. 13 is a front elevational view of the upper portion. In this view, there is shown notch 29 in lower edge 27 of front wall 24. This notch cooperates with notch 33 in the lower edge of the rear wall to permit a person to grip a set of a refill chambers and remove these chambers. Interlocking projection 41 also is shown.

Figure 14:
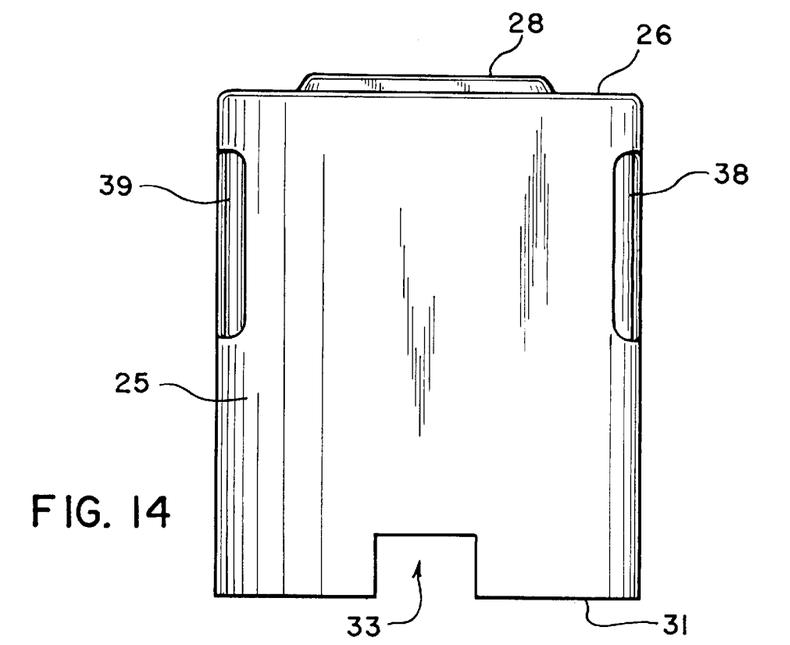
FIG. 14 is a rear elevational view of the upper portion.
Figure 15:
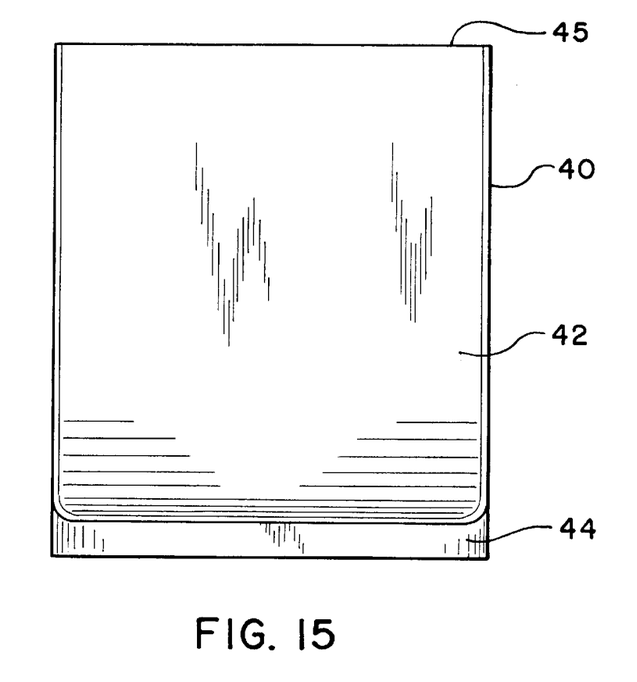
FIG. 15 is a front elevational view of the bottom portion.

FIG. 14 shows a rear elevational view of the upper portion with notch 33. This notch assists in the removal of a cartridge from the upper portion. Lower edge 31 is the bottom of the walls of the upper portion. FIG. 15 shows a front view of the lower portion. This has a top edge 45, front wall 42 and front 44.

FIG. 15 is an elevational view of the lower portion. There are no notches in the lower portion.

Figure 16:
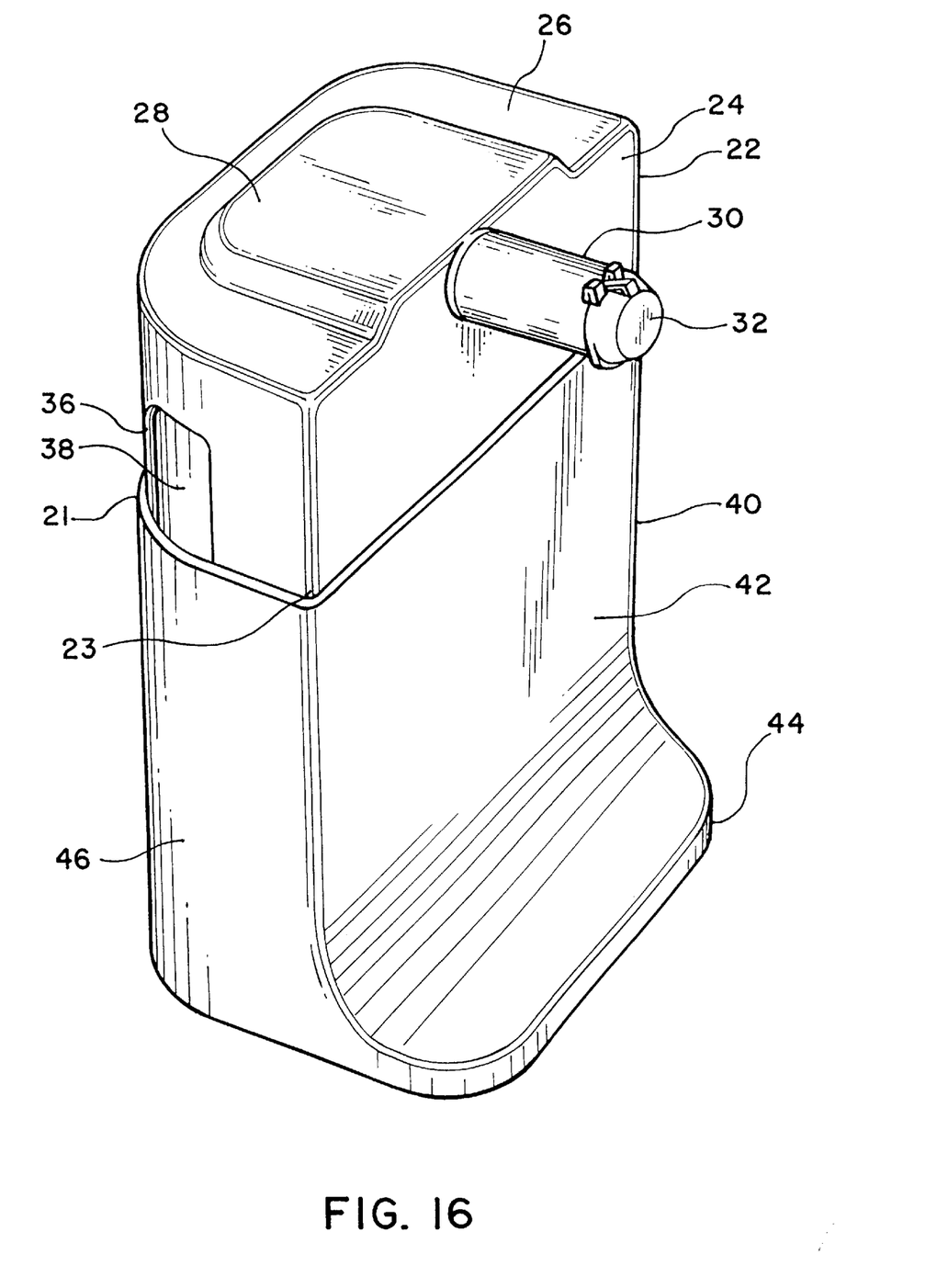
FIG. 16 is a perspective view of the dispenser in a depleted condition.

FIG. 16 shows the dispenser when it has been depleted of the substances in the chambers. The fill status of the chambers also can be viewed through aperture 36. At this time, the upper portion is separated from the lower portion by extending the upper portion from the lower portion and pushing in on front wall 25 to disengage the interlock projections. Once separated, the set of chambers in the upper portion are gripped through the notches in the front and rear walls and removed from the upper portion. A new refill set of chambers then is inserted into the upper portion and the lower portion put into place. The seals on the chambers are automatically opened by the described cutters. The dispenser then is ready for use.

This dispenser is useful for dispensing viscous materials such as pastes and gels. In the usual instance the substances to be dispensed are not compatible and must be kept separate until the time of use. These substances include adhesives, personal care products such as for hair treatments and oral care products such as dentifrices and tooth and gum treatments. The dispenser is useful for substances that are not compatible, such as being reactive or which are not storage stable and must be kept separate until the time of use.

This specification sets out the preferred embodiments of the present dispenser. Included are the variations that can be made in adjusting the components during manufacture and producing units in a larger or smaller size. These are all considered to be within the concepts disclosed in this specification.

We claim:

1. A multi-chamber dispenser for flowable substances comprising an upper portion and a lower portion, said upper portion having a plurality of chambers containing said flowable substances, each chamber having an exit end with a reduced dimension exit opening, said exit opening connected by a channel on said upper portion to a dispenser exit, each channel separated by a common single divider wall and receiving said flowable substances in a first direction and flowing said flowable substances in a second direction the other end of said chambers closed by a piston moveable within said chambers, said lower portion having a plurality of piston rods at least equal in number to said chambers, each of said piston rods extending into one of said chambers, said exit opening of each chamber being adjacent a peripheral wall of each chamber and adjacent to each other to flow said flowable substances in said first direction and into the channel connecting the exit end of each chamber with the exit opening and then in a second direction in said channel toward said exit opening.

2. A multi-chamber refillable dispenser as in claim 1 wherein said exit opening of each chamber comprises a chamber projection, said chamber projection located adjacent said peripheral wall of each chamber.

3. A multi-chamber refillable dispenser as in claim 1 wherein at least two portions of said piston rods are proximate an inner surface of a chamber wall whereby said piston rods are stabilized in said chamber.

4. A multi-chamber refillable dispenser as in claim 1 wherein the upper portion has an upper wall, an inner surface of said upper wall having an upper portion seal means for each chamber, each seal means in communication with one of said channels connecting to said dispenser exit.

5. A multi-chamber refillable dispenser as in claim 4 wherein said seal means comprises at least one projection extending from the inner surface of said upper wall and which receives at least one chamber projection.

6. A multi-chamber refillable dispenser as in claim 4 wherein each seal means includes a cutter to cut a seal on the exit opening of each chamber.

7. A multi-chamber refillable dispenser as in claim 6 wherein said cutter comprises a cutter projection within said seal means and extending downwardly from the inner surface of said upper wall with a cutting section projecting downwardly from the inner surface of said upper wall, said cutter section at least partially contained within said cutter projection.

8. A multi-chamber refillable dispenser as in claim 1 wherein the upper surface of said pistons is deformable whereby said piston top surface wall adapts to the shape of the top of said chambers.

9. A multi-chamber refillable dispenser as in claim 1 wherein said chambers have projections on an edge on an exterior surface on an upper part, said projections causing said refill chambers to fit into said upper portion in a single orientation.

10. A multi-chamber refillable dispenser as in claim 1 wherein said upper portion has an upper wall and side walls extending downwardly from said upper wall, said side walls having apertures adjacent the upper portion of each refill chamber.

11. A multi-chamber refillable dispenser as in claim 1 wherein said upper portion has an upper wall and side walls extending downwardly from said upper wall, a front wall and a rear opposing wall having a notch opening adjacent a lower edge to expose a lower portion of said chambers.

12. A multi-chamber refillable dispenser as in claim 1 wherein said upper portion has an upper wall, said upper wall having a centrally raised portion to define a push pad for actuating said dispenser.

13. A multi-chamber refillable dispenser as in claim 1 wherein said upper portion and said lower portion each have at least one mating corner when said upper portion and said lower portion are interfitted, said at least one mating corner of said upper portion and said lower portion fit in a close relationship to thereby stabilize said lower portion in said upper portion.

14. A multi-chamber dispenser for flowable substances comprising an upper portion and a lower portion, said upper portion having a plurality of chambers containing said flowable substances, each chamber having an exit end, said exit end connected to a seal means on said upper portion, each seal means connected by a channel to an exit opening, said seal means comprising at least two adjacent first projections depending from an inner surface of an upper wall of said upper portion, a chamber projection on said exit end of each of at least two chambers, said chamber projections fitting into the at least two adjacent first projections depending from said upper wall, and an other end of each chamber closed by a moveable piston, said lower portion having a plurality of piston rods equal in number to the number of said chambers, said piston rods fitting into said chambers to contact said pistons.

15. A multi-chamber refillable dispenser as in claim 14 wherein at least two portions of said piston rods are proximate the inner wall of said chambers to thereby stabilize said piston rods in said chambers.

16. A multi-chamber refillable dispenser as in claim 14 wherein the second projections are located adjacent a wall of each chamber.

17. A multi-chamber dispenser as in claim 16 wherein the second projections on each chamber are adjacent to each other.

18. A multi-chamber dispenser as in claim 14 wherein said seal means comprises a cutter extending from the inner surface of said upper wall and contained within said seal means, said cutter comprises a cutter projection within said seal means extending from the inner surface of said upper wall with a cutter section projecting downwardly from the inner surface of said upper wall, said cutter section at least partially contained within said cutter projection.

19. A multi-chamber refillable dispenser as in claim 14 wherein the upper surface of said pistons is deformable whereby said piston surface will adapt to the shape of the top of said chambers.

20. A multi-chamber refillable dispenser as in claim 14 wherein said chambers have projections on an edge on an exterior surface on an upper part, said projections causing said refill chambers to fit into said upper portion in a single orientation.

21. A multi-chamber refillable dispenser as in claim 14 wherein said upper portion has side walls extending downwardly from said upper wall, said side walls having apertures adjacent the upper portion of said chamber.

22. A multi-chamber refillable dispenser as in claim 14 wherein said upper portion has side walls extending downwardly from said upper wall, opposing walls having a notch opening adjacent a lower edge to expose a lower portion of said chambers.

23. A multi-chamber refillable dispenser as in claim 14 wherein said upper wall has a centrally raised portion to define a push pad to actuate said dispenser.

* * * * *